United States Patent [19]

Katz et al.

[11] 4,180,560

[45] * Dec. 25, 1979

[54] INERT CORE IMPLANT PELLET

[75] Inventors: Martin Katz, Los Altos Hills; John S. Kent, Palo Alto, both of Calif.

[73] Assignee: Syntex Corporation, Palo Alto, Calif.

[*] Notice: The portion of the term of this patent subsequent to Jun. 27, 1995, has been disclaimed.

[21] Appl. No.: 903,284

[22] Filed: May 5, 1978

Related U.S. Application Data

[63] Continuation of Ser. No. 735,727, Oct. 26, 1976, Pat. No. 4,096,239, which is a continuation-in-part of Ser. No. 572,031, Apr. 28, 1975, abandoned.

[51] Int. Cl.² .......................... A61K 9/22; A61K 9/24
[52] U.S. Cl. ........................................ 424/21; 424/16; 424/19; 424/22
[58] Field of Search ........................... 424/19–22

[56] References Cited

U.S. PATENT DOCUMENTS 4,096,239   6/1978   Katz et al. ............................. 424/21

OTHER PUBLICATIONS

Cooney A. I. Ch. E. Jl. vol. 17, No. 3, pp. 754–756, "Slow Dissolution of Implanted Beds of Spherical Particles as a Method for Prolonged-Release Medication".

*Primary Examiner*—Shep K. Rose
*Attorney, Agent, or Firm*—Tom M. Moran; Joseph I. Hirsch

[57] ABSTRACT

A novel spherical implant pellet containing estradiol, estradiol benzoate, or mixtures thereof as the sole active ingredients which exhibits a substantially constant drug release rate over a timer period and substantially abrupt termination of drug release at the end of the time period is prepared which has an inert spherical core of a diameter of about 2–10 mm and a uniform coating of about 0.05–1 mm completely covering the core, the coating comprising about 5–99% suitable carrier and 1–95% drug. A drug may be administered at a constant rate over a chosen period by implanting the novel pellet and the release is substantially abruptly terminated at the end of said period without removing the pellet.

4 Claims, No Drawings

INERT CORE IMPLANT PELLET

This is a continuation, of application 735,727 filed Oct. 26, 1976, U.S. Pat. No. 4,096,239 which in turn is a continuation-in-part of U.S. Pat. Application Ser. No. 572,031 filed Apr. 28, 1975, now abandoned.

BACKGROUND OF THE INVENTION

1. Field of the Invention

This invention relates to a novel, spherical, subcutaneously implantable pellet containing estradiol, estradiol benzoate, or mixtures (hereafter sometimes referred to as the drug) thereof which exhibit a substantially constant release rate over a period of time and a substantially abrupt termination of drug release at the end of that period of time. The pellet has a biocompatible, spherical inert core which is uniformly covered by a drug/carrier composition, the diameter of the core being more than 50% of the diameter of the spherical pellet. The invention further relates to a process for administering the drug at a substantially constant rate to an animal by implanting the novel pellet of this invention into the animal.

2. Prior Art

A substantial body of literature exists which describes dosage forms of drugs which exhibit some type of controlled release mechanism. Useful discussions of prolonged action oral pharmaceuticals as well as implanted solid drug pharmaceuticals are discussed in *Remington's Pharmaceutical Sciences*, 14th Edition, Chapter 89 entitled "Prolonged Action Pharmaceuticals" by Burton E. Ballard and Eino Nelson, Mack Publishing Company, 1970 as well as in *Patents For Prolonged Action Dosage Forms*, Edward Stemple, Drug and Cosmetic Industry, 98, Nos. 1 and 2, January, 1966, pgs. 44–46 and 118–123 and February, 1966, pgs. 36–38, 139–142, 145, 146, and 148. A discussion of recent theories behind absorption of an implanted solid drug are discussed in "Absorption of Implanted Solid Drug", Ballard and Nelson, J. Pharm. Sci., Vol. 51, No. 10, pgs. 915–924, October, 1962. From this background information as well as the patent literature it is clear that subcutaneous pellet implants are known in the art and generally may be categorized as either diffusion matrix pellets, diffusion barrier pellets, or dissolution pellets.

Examples of diffusion matrix implants may be found in U.S. Pat. Nos. 3,565,991 to Short; 3,577,512 to Sheppard et al; and 3,737,521 to Born. In these patents a drug is dispersed throughout a polymer which is implanted in the body and this drug is leached or diffuses from the polymer matrix in which it is dispersed. Generally the diffusion matrix formulation results in the release rate of the drug which may be substantially constant over a first period of time but which eventually diminishes as the drug is released from the formulation. In many formulations of this type substantial amounts of drug may remain in the matrix even after it has become inactive.

Representative descriptions of dissolution implant pellet formulations may be found in U.S. Pat. No. 3,428,729 to Anderson et al and U.S. Pat. No. 2,895,875 to Klette. The Anderson et al patent is a diethylstilbestrol implant formulation which shows a decreasing rate of release, whereas the Klette patent discloses an implant which comprises an inner core of coarse hormone crystals surrounded by a layer of smaller water soluble hormone crystals in a binder such as methylcellulose. The Klette invention results in a shock like effect when the outer small particles are quickly dissolved in the body fluid but a prolonged effect due to the coarse inner crystals. Thus, there are two entirely different rates of release, whereas in a preferred aspect of this invention, a substantially constant release rate may be obtained. Dissolution pellets exhibit the disadvantage of a decreasing rate of release as time progresses. Also more drug is utilized in the pellet than is delivered at an effective level because of the decreasing rate. A cattle bolus having an inert, high density core and active ingredients surrounding it is described in British Pat. No. 936,386.

An example of a diffusion barrier implant may be found in U.S. Pat. No. 3,279,996 to Long and Folkman. In this design a drug is placed in the lumen of a tube of polydimethysiloxane and the ends of the tube are sealed. The tubing wall thickness and surface area of the tube determine the rate of release for a given drug.

With any of the known prior art dosage forms certain difficulties have been encountered. For example in the case of dissolution pellet formulation it is found that the rate of release changes substantially over the period of time in which the pellet is placed in the animal body. It is believed that the declining rate of release is due at least in part to a decrease in the size of the pellet and a consequent decrease in the area of the pellet available to be acted upon by the body. Thus, the rate of release of the drug from the pellet is very high at the beginning of the implantation but becomes very low as the time progresses. In order to administer an average amount over the time period the pellet is designed to give a greater amount than is needed over the first period of time and substantially less than the optimum amount over later period of time when the release rate decreases substantially.

On the other hand in the diffusion matrix formulation although the rate of drug release might be maintained at a fairly constant rate, these generally have the disadvantage that there is often a large quantity of drug which is left in the matrix which does not diffuse out at the optimum rate but leaches out only very slowly. Thus, this particular type of implant may utilize more drug than is required in order to get the proper release rate. This results in an economically disadvantageous product since more drug is employed in the pellet than is actually administered to the animal.

The diffusion barrier implant described in the Long and Folkman patent has the disadvantage of being difficult to prepare in that the active ingredient must be placed inside the small diameter tube, a mechanically difficult task. Further polysiloxane is expensive.

It is generally known that pellet implants having the shape of a cylinder or a disc may be used for the treatment of animals. For example Synovex ®H, a commercial product marketed by Syntex Laboratories is a cylindrical shape, while U.S. Pat. No. 3,499,445 to Reed describes a disc shaped depot which is adapted for encasement by a foraminous device and subsequent subcutaneous implantation.

It has now been discovered, however, that it appears that the body reacts adversely to subcutaneous implants which have sharp edges on the implant such as the corners of discs or cylinders and that a greater degree of encapsulation of the implant is seen which causes the drug to be released from the implant relatively unevenly. Further, the disc used as a subcutaneous implant offers certain disadvantages in that it is difficult to manufacture a disc which exhibits sufficient structural integrity to withstand the forces of the body acting on the disc. Because of this lack of structural integrity, the Reed U.S. Pat. No. 3,449,445 patent teaches that its necessary to enclose a disc by a protective device so that when the disc disintegrates the pieces will be retained by the foraminous encasing device. Further, it is nearly impossible to implant a disc by any means other than by surgery since the pressures on the discs of questionable structural integrity may result in the disc breaking before even being implanted if a simple injection device is used such as that described in U.S. Pat. No. 2,761,446.

Surprisingly, it has been found that by administering estradiol, estradiol benzoate, or mixtures thereof according to the process and composition of this invention, less total drug is needed to produce a weight gain equivalent or better to that obtained by using a mixture of estradiol benzoate and progesterone (SYNOVEX-S).

The uniquely formulated pellet of this invention offers the following advantages over the prior art:
The pellet exhibits a substantially constant rate of release of drug over the life of the pellet;
There is an abrupt termination of drug release at the end of the life of the pellet;
Substantially no active drug remains in the pellet at the site of implantation at the end of the life of the pellet;
There is less encapsulation of the pellet;
The pellet is easily prepared;
A reduction of total administered dose of drug may be attained;
The pellet may be easily implanted using simple injection devices, surgery is not required;
Surgery is not required to terminate administration of the drug.

SUMMARY OF THE INVENTION

The primary aspect of this invention is a subcutaneously implantable spherical pellet which exhibits a substantially constant rate of drug release over a first time period and a substantially abrupt termination of drug release at the end of said time period, the pellet comprising a biocompatible, inert spherical core having a diameter of about 2 mm to about 10 mm and a biocompatible, biosoluble coating having a substantially uniform thickness of about 0.05 mm to about 1 mm intimately adhering to and completely covering the inert core, the composition of the coating being about 10% to 95% of a pharmaceutically acceptable carrier, particularly polyethylene glycol (PEG) having a molecular weight of 3,000–20,000 or mixtures of PEG and cholesterol, and about 5 to 90% of estradiol, estradiol benzoate, or mixtures thereof. Preferably, the inert core is biosoluble and is absorbed by the animal's system.

The process of this invention comprises administering estradiol, estradiol benzoate, or mixtures thereof to an animal at a substantially constant rate by subcutaneously implanting the pellet of this invention in the animal to produce a greater than normal weight gain in the animal. Thereafter the animal may be slaughtered.

PREFERRED EMBODIMENTS

Composition

The spherical pellet of this invention is valuable in the administration of estradiol, estradiol benzoate, or mixtures thereof to animals of any type including mammals, birds, or others, but is preferred in cattle, especially steers. Because of its acceptance and availability estradiol benzoate is preferred, but since it is well established that estradiol is one of the first metabolism products, it too can be employed as well as mixtures of the two.

Broadly, this invention may be viewed as a spherical, subcutaneously implant pellet which exhibits a substantially constant rate of estradiol, estradiol benzoate, or mixtures (referred to hereafter as the "drug") delivery over a time period and an abrupt termination of drug release at the end of that time period. The implant pellet may be formulated to deliver the drug at a substantially constant rate over a period of anywhere from 5 days to more than a year, preferably 30–100 days, e.g. 60. To obtain the constant rate of drug delivery and the abrupt termination of drug release, the implant comprises a biocompatible, inert spherical core having a diameter of about 2 mm to about 10 mm, the core having a biocompatible coating with a substantially uniform thickness of about 0.05 mm. to about 1 mm. intimately adhering to and completely covering the inert core. The composition of the coating comprises a substantially homogeneous mixture of about 10%w to about 95%w of a pharmaceutically suitable carrier and about 5%w to 90%w of the drug, the thickness of the coating and its composition determining the time period and the rate of release of the drug.

It has been discovered that there is a greater degree of encapsulation in the animal body in the case of pellets having sharp corners such as discs or cylinders. Also, the structural integrity of the pellet of this invention must be such that it can withstand injection pressure from simple injection needle devices. Further, if the core is not substantially spherical, the coating may not be applied uniformly in the preparation of the pellet and thus the rate of release of the drug in the coating may be adversely affected and will not be constant over the time period desired. For these reasons it is important that both the inert core and the finished pellet be substantially spherical. The spherical core is inert in itself, that is, there is substantially no drug in the core. If there is drug in the core, of course this means that the rate of release will not be substantially constant over the period of time as desired. Further, the inert core must be biocompatible in that it is non-toxic to the body in which it is implanted and the body does not otherwise react adversely to it. The core materials may be non-dissolving or dissolving materials. Examples of non-dissolving materials include glass, biocompatible polymers such as cellulose acetate, methylmethacrylate or other acrylics, nylon, polypropylene, silicone rubber, SBR copolymers, and the like. Representative dissolving material include polyethylene glycols such as POLYOX ® (Union Carbide) or KLUCEL ® (Hercules) and sugar-starch beads. Using a dissolving core has the advantage that once the drug has been released from the outer layer, the core is absorbed into the animal system and thus there is nothing left of the implant at all. This is particularly important in implanting domestic stock animals for weight gain or disease treatment, which animals are eventually processed for food consumption by humans since if the drug and core have all been absorbed and metabolized by the body there is nothing left to interfere with the processing system or to be removed before processing. This of course results in savings of labor during the food processing procedure.

Generally the spherical core must be of a size so that the resulting pellet may be readily injected into the animal using equipment which is generally known in the art. The diameter of the core will thus generally be from about 2 mm. to about 10 mm. and preferably will be about 2 mm to about 3 mm.

To maintain a substantially constant rate of release in the preferred, inert core formulation of this invention, the diameter of the inert core is at least half the diameter of the final spherical implant and preferably will be at least about ¾ of the diameter of the final spherical implant. Thus if the inert core has a diameter of 2.4 mm, the final sphere will preferably have a diameter of 3.2 mm or less, but greater, of course, than 2.4 mm. By "substantially constant" rate of release is meant that the rate of release decreases by less than about 50% from the start of the implantation to the termination of the release of drug.

A method may be employed to assist in maintaining a substantially constant rate of release per sphere especially if the diameter of the inert core is between 50%–75% of the diameter of the final sphere. In this aspect of the invention it is possible to compensate for the slight decrease in release rate per sphere which results as the diameter of the sphere decreases by adjusting the composition of the coating so that the active ingredient is released at a greater rate per unit area as the radius decreases. This can be performed by using a multi-layer technique wherein, for example, the percentage of water soluble components such as polyethylene glycol is altered so that there are higher concentrations in the inner layers to increase the dissolution and compensate for the decrease in surface area. Alternatively, gradually increasing concentrations of drug may be used in the innermost layers of the coating to compensate for the gradually decreasing surface area since solution rate is usually proportional to concentration. The selection of the proper alternative depends on a complex interrelationship of the solubility and concentration of both the drug and the coating components. In any case, the formulator is capable of making these adjustments to provide uniform drug release by a gradual change in the composition of the layers of the coating to provide increased drug release, either by increased drug concentration and/or increased soluble coating components, to compensate for the decreased surface area. But even with this alternative multi-layer technique it is preferable to utilize an inert core which accounts for at least half of the radius of the implanted sphere.

As disclosed previously the inert core may be about 2–10 mm in diameter and preferably about 2–3 mm. The finished sphere having the uniform coating covering the inert core will generally be about 2.1–12 mm in diameter and preferably will be about 2.2 to about 3.5 mm. Thus, the uniform layer (or layers as the case may be) adhering to the inert core will range from about 0.05 mm to about 1 mm thick and preferably will be about 0.1 mm to about 0.5 mm thick. For example, if the inert core is 2.0 mm in diameter (1.0 mm radius) and the uniform layer is 0.05 mm, the diameter of the finished sphere is 2.1 mm (2[1.0+0.05]=2.1).

In order to obtain the constant rate of release in the pellet of this invention, a coating having a substantially uniform thickness is layered onto the inert spherical core. It is important that the thickness of the coating be substantially uniform around the inert core so that the calculated rate of release will be obtained. Further, it is important that the coating intimately adheres to the core to maintain structural integrity and prevent the release rate from fluctuating. "Intimately adhering" to the core means that the coating layer will stay on the inert core during the entire time period during which the drug is to be released in a manner so that substantially none of the coating falls off to adversely effect the rate of release of this drug.

The coating containing the drug must completely cover the inert core so that the rate of release calculated for the size sphere employed can be obtained. Also, if the inert sphere is not completely covered by the coating containing drug there is a greater likelihood that the coating will deteriorate and be separated from the inert sphere. This of course would adversely effect the rate of release and instead of giving a constant rate would result in a varying rate.

The carrier which may be utilized in the coating of this invention may be any suitable carrier but of course must be biocompatible with the animal which is being treated, that is it may not be toxic to the animal or otherwise adversely affect the metabolism of the animal. Further, the coating must be biosoluble, that is it must dissolve in the body fluids which act upon the pellet where it is implanted in the body. Thus, it can be seen that the carrier which is used to coat the inert sphere is a binder as well as a dissolution rate modifier for the drug. It is a binder in that it must properly adhere to the inert core while maintaining the structural integrity of the coating and is a dissolution rate modifier in that it effects the rate at which the drug is released from the implanted core.

For proper adherence to the inert core at least about 5% of the carrier is needed in the uniform outer coating, and to obtain a therapeutically effective dose of the drug at least about 10% of the coating should be the drug. Thus, the range of the composition of the outer coating is about 10%w to about 95%w of the drug and about 5%w to about 90% of the carrier. Preferred is a mixture of about 20%w to about 90%w active agent (especially 30–90%) and about 10%w to about 80%w (especially 10–70%) of the carrier.

Representative carriers which may be used for the purpose of this invention include cholesterol, solid polyethylene glycols (PEG), high molecular weight fatty acids and alcohols such as stearic acid or cetyl alcohol, biosoluble waxes, cellulose derivatives such as carboxymethocellulose, and solid polyvinyl pyrrolidone. Depending upon the carrier and drug combination used, the drug may be absorbed at a faster or slower rate than the drug would be if it were coated on the sphere alone. For example, PEG generally speeds up the rate of release while cholesterol generally slows down the rate of release compared to PEG. Because of availability, compatibility with most animals, and adherence properties, solid polyethylene glycols having molecular weights in the range of about 3,000 to about 20,000, especially PEG 6000–7500, e.g. CARBOWAX ® 6000, are particularly preferred. Mixtures of PEG with cholesterol having a ratio of about 5:1 to about 115 are particularly valuable. Generally as the percentage of polyethylene glycol increases the rate of release of the drug will also increase since polyethylene glycol is substantially more soluble in water and the fluids in the animals then are the drugs.

Process of Preparation

Generally, the process for preparing the spherical, inert core, pellet implant of this invention may be performed by any of the film coating techniques known in the art including a fluidized bed method, the Wurster Air Suspension Coating method, the spray pan method or a programmed automated spray pan method. These processes are broadly discussed in Chapter 88 of *Remington's Pharmaceutical Sciences*, 14th Edition, Mack Publishing Company, 1970, pp. 1685–1688 and as much of that disclosure as is pertinent is incorporated herein by reference.

Broadly stated, the process involves dissolving the drug and carrier in a suitable solvent, contacting the inert spheres with the resulting solution to thoroughly wet the spheres, then evaporating the solvent from the solution so that the carrier and drug combination remains uniformly coated on the inert spheres. Thus the biologically active agent/carrier combination which is to be coated onto an inert sphere must have solution properties in a solvent or combination of solvents suitable for spray coating. Generally high formulation concentrations in the coating solvent have the advantage of a shorter coating time and use of less solvent, but high formulation concentrations tend to yield a less uniform product and thus it is preferable to use lower concentrations. Preferably the concentration of the drug and carrier will be less than 50% and preferably will be between about 15%w to 25%w in the solvent.

During the coating process the spheres used for the inert cores are kept in constant movement so that the drug/carrier solution is uniformly coated on the spheres, then the solvent is removed by evaporation, generally blowing hot air across the spheres while keeping them in constant motion, again to assure uniformity of coating. The spheres are kept in constant motion by employing a circular spray pan which is constantly and uniformly revolved at a uniform rate or by using an air suspension column in which the spheres are suspended in an air stream. The solvent is applied intermittently along with the hot air in a pre-set spray/dry cycle.

The coating solvent is important in the process of this invention since it must have the proper solubility characteristics for the formulation as well as the proper drying characteristics to provide smoothness of the coating. Examples of acceptable coating solvents for coating have been acetone, chloroform, methylene chloride, isopropyl alcohol, ethanol, methanol, propanol, tetrahydrofuran, trichloroethylene, dioxane, dimethylformamide, and mixtures of these.

It has been discovered that the process is greatly improved and results in a superior product if the solvent combination employed is chloroform and isopropyl alcohol (IPA) at a ratio of about 1:4 to 2:1, preferably about 1:3 to 1:1, respectively, the drug and carrier such as PEG and cholesterol being dissolved first in the chloroform and the IPA being added thereafter.

PROCESS OF ADMINISTERING DRUG

Generally the process of administering drugs utilizing the pellet of this invention comprises implanting at least one of the above described pellets into an animal so that a therapeutically effective amount of the drug is released to the animal at a substantially constant rate over a given time period, the drug being substantially fully released at the end of that time period.

A therapeutically effective amount is that amount needed to effect the desired result, i.e. weight gain, when implanted either alone or in combination with other similar pellets. Generally a plurality of pellets will be implanted successively or simultaneously and thus the pellets are preferably packaged as a group sufficient for one animal. The rate of release in the animal will depend on the individual animal, implantation site, drug concentration, carrier, etc., and may vary over a broad range. Generally, if the same number of pellets of the same formulation are injected into the same species of animal the release rate as well as the termination will be the same, with allowance for small variations (e.g., less than 5%) between individual animals.

In order to administer the necessary dosage requirement to the animal for producing weight gain, it is usually necessary to implant a plurality of the spheres. The process generally involves implanting an animal over a given period of time using the above described implant so that a constant amount of the drug is administered over the period of time, the drug being fully released at the end of that period of time, feeding the animals a normal diet while administering the drug. The implant, of course, is not removed to terminate administration of the drug. A second time period may be utilized to assure that the drug is entirely metabolized by the animal so that there is no drug left at levels which might be harmful to humans if they were to eat the meat of the animals treated. The animal may be slaughtered after the given period of time of implantation. If the inert core is soluble in the animal in which it is implanted and is absorbed after the given period of time the animal need not be treated any further before processing. However, if the inert core is not absorbed and stays in the animal it will have to be removed prior to processing such as slaughtering and processing. For example, if the pellets are implanted in the animals ears the ears are merely cut off and discarded.

The basic premise behind the use of estradiol benzoate, estradiol, or mixtures thereof in a domestic stock animal is that the animal will gain more weight during a given time period by using the drug.

The weight gain may be due to increased consumption by the animal, increased food efficiency, or both. Increased consumption is advantageous, especially to a feed lot operator, since he is trying to maximize the weight gain over a specific time period and is willing to feed the animals greater quantities of food over a shorter period of time if they will fatten faster. Increased consumption may be seen using the implantable pellet of this invention, especially with male animals. Food efficiency (%) is defined as $$\frac{\text{weight gained by animal}}{\text{food consumed by animal}} \times 100\%.$$

Thus the process of producing a weight gain is a process for increasing the food efficiency of the animal. The commercial advantage of estradiol or estradiol benzoate to increase the food efficiency is that it allows a raiser of cattle, sheep, pigs, and the like to produce more marketable meat from the feed purchased.

In ruminant animals such as cattle which exhibit growth throughout their life, the pellet implant of this invention may be implanted during any phase of the animal's life and a weight gain may be realized. Thus the process of this invention is adaptable to the custom of the cattle raiser concerned. For example, in the case of raising "vealers", calves raised and slaughtered prior to sexual maturity to produce veal, the pellet is implanted in the calf early in its life and the calf is fed and maintained for the necessary period of time after which it is slaughtered. The calf as treated will show a rate of growth which is greater than a calf which has not received an implant. On the other hand the pellet of this invention may be implanted in cattle, preferably steers, which are past puberty and a greater than normal weight gain will also be seen. Such post-puberty cattle include dairy cattle beef cattle, or crossbreeds of the two.

Implantation is done by any method known to be useful for subcutaneous implantation and may be done surgically or preferably, by injection using a needle implanter such as that taught in U.S. Pat. No. 2,761,446. The spherical pellets of this invention lend themselves to ready injection using the needle type implanter. Generally the pellets will be injected into an area in the animal which will not physically harm or bother the animal's eating habits. For example in the case of heifers and steers the pellets are injected into the animals ears, neck or back regions. In the case where the inert core is a non-dissolving material, it is preferred to inject the spheres in a part of the animal which may be easily removed prior to slaughter, e.g. the ears. On the other hand, if the inert core is of a biosoluble material, the spheres may be implanted elsewhere, e.g. the back, since the core will be absorbed prior to slaughter anyway.

The following examples are given by way of illustration of representative formulations and process parameters which are representative of various aspects of this invention. However, the examples are not to be read in a limiting sense and are to be read as illustrative only.

EXAMPLE I—FORMULATION FOR WEIGHT GAIN IN CATTLE 18.0 gm of estradiol benzoate, 9.0 gm. of cholesterol, and 3.0 gm. of polyethylene glycol 6000 were dissolved in 240 milliliters of chloroform after which 60 milliliters of isopropyl alcohol was added. This solution was used to coat 40 gm. of cellulose acetate spheres, each sphere having an average diameter of 2.5 mm and average weight of 10.5 mg. The spheres were placed in a 5 inch diameter glass coating pan and coated using a Badger air atomization spray gun, a hot air blower and dual timer at the following setting:
 air pressure=20 pounds per square inch
 spray-dry cycle=5:15 seconds
 pan bed temperature=37° C.
 pan rotation=36 revolutions per minute
The spheres were coated to give an average weight per sphere of 9.440 mg. of which 5.664 mg. is estradiol benzoate, 2.832 mg. is cholesterol and 0.944 mg. is polyethylene glycol 6000.

EXAMPLE II—FORMULATION FOR WEIGHT GAIN IN CATTLE 30.0 gm of estradiol benzoate, 5.0 gm. of cholesterol, and 15.0 gm. of polyethylene glycol 6000 were dissolved in 200 milliliters of chloroform after which 50 milliliters of isopropyl alcohol was added. This solution was used to coat 40 gm. of cellulose acetate spheres, each sphere having an average diameter of 2.8 mm and average weight of 15.2 mg. The spheres were placed in a 5 inch diameter glass coating pan and coated using a Badger air atomization spray gun, a hot air blower and dual timer at the following setting:
 air pressure=20 pounds per square inch
 spray-dry cycle=5:15 seconds
 pan bed temperature=37° C.
 pan rotation=36 revolutions per minute
The spheres were coated to give an average coating weight per sphere of 6.556 mg. of which 3.93 mg. is estradiol benzoate, 0.656 mg. is cholesterol and 1.97 mg. is polyethylene glycol 6000.

EXAMPLE III—FORMULATION FOR WEIGHT GAIN IN CATTLE 50.0 gm of estradiol was dissolved in 500 ml. of tetrahydrofuran, and 50.0 gm. of polyethylene glycol 6000 was dissolved in 250 milliliters of chloroform after which the two solutions were combined. This solution was used to coat 40 gm. of cellulose acetate spheres, each sphere having an average diameter of 2.5 mm and average weight of 10.5 mg. The spheres were placed in a 5 inch diameter glass coating pan and coated using a Badger air atomization spray gun, a cold air blower and dual timer at the following setting:
 air pressure=5:10 seconds
 pan bed temperature=25° C.
 pan rotation=36 revolutions per minute
The spheres were coated to give an average weight per sphere of 9.95 mg. of which 4.975 mg. is estradiol and 4.975 mg. is polyethylene glycol 6000.

We claim as our invention:

1. A solid, spherical, subcutaneously implantable pellet for producing a greater than normal weight gain in ruminants, which implantable pellet exhibits a substantially constant rate of release of active agent over a given time period and an abrupt termination of drug release at the end of said time period, said pellet comprising
 (a) a biocompatible, inert, spherical core having a diameter of about 2 mm to about 10 mm and
 (b) at least one biocompatible, biosoluble coating having a substantially uniform thickness of about 0.05 mm to about 1.0 mm intimately adhering to and completely covering said inert core, the composition of said coating comprising a substantially homogeneous mixture of (i) about 5% weight to about 90% weight of estradiol, estradiol benzoate, or mixtures thereof as the sole active agent(s), and (ii) about 10% weight to about 95% weight of a pharmaceutically suitable carrier which is solely a polyethylene glycol having a molecular weight of about 3000 to about 20,000, said inert, spherical core being at at least half the diameter of said spherical, implantable pellet.

2. The pellet of claim 1 wherein said polyethylene glycol has a molecular weight about 6000 to 7500.

3. A process for administering estradiol, estradiol benzoate, or mixtures thereof to a ruminant over a given period of time to provide a greater than normal weight gain, which process comprises subcutaneously implanting at least one spherical pellet comprising
 (a) a biocompatible, inert, spherical core having a diameter of about 2 mm to about 10 mm and
 (b) at least one biocompatible, biosoluble coating having a substantially uniform thickness of about 0.05 mm to about 1.0 mm intimately adhering to and completely covering said inert core, the composition of said coating comprising a substantially homogeneous mixture of (i) about 5% to about 90% weight of estradiol, estradiol benzoate or mixtures thereof as the sole active agent(s), and (ii) about 10% weight to about 95% weight of a pharmaceutically suitable carrier which is solely a polyethylene glycol having a molecular weight of about 3000 to about 20,000, the diameter of said inert spherical core being at least half the diameter of said spherical implantable pellet, said active agent(s) being released at a substantially constant weight-gain producing rate over said given time period, said agent(s) being substantially fully released at the end of said given time period and substantially none of said active agent(s) being released from said pellet after said given time period.

4. The process of claim 3 wherein said polyethylene glycol has a molecular weight of about 6000 to 7500.

* * * * *